United States Patent [19]

Pilgram et al.

[11] 4,184,867
[45] Jan. 22, 1980

[54] CYCLOALKANECARBOXANILIDE DERIVATIVE HERBICIDES

[75] Inventors: Kurt H. G. Pilgram; Richard D. Skiles, both of Modesto, Calif.

[73] Assignee: Shell Oil Company, Houston, Tex.

[21] Appl. No.: 876,599

[22] Filed: Feb. 10, 1978

Related U.S. Application Data

[63] Continuation-in-part of Ser. No. 761,515, Jan. 21, 1977, abandoned.

[51] Int. Cl.$^2$ .................... A01N 9/12; A01N 9/14; C07C 103/737
[52] U.S. Cl. .................... 71/98; 71/103; 260/556 B; 260/557 R
[58] Field of Search ............ 260/556 B, 557 R, 562 P; 71/98, 103, 118

[56] References Cited

U.S. PATENT DOCUMENTS

| | | | |
|---|---|---|---|
| 3,211,544 | 10/1965 | Dubrovin | 71/118 |
| 3,328,156 | 6/1967 | Hopkins | 71/118 |
| 3,407,056 | 10/1968 | Schwartz | 71/118 |
| 3,484,485 | 12/1969 | Schwartz | 260/557 R |
| 3,660,486 | 5/1972 | Thiele | 260/562 P |
| 3,753,679 | 8/1973 | Singhal | 71/98 |
| 4,090,865 | 5/1978 | Baker | 260/562 P X |

FOREIGN PATENT DOCUMENTS

| | | | |
|---|---|---|---|
| 749581 | 10/1970 | Belgium | 71/118 |
| 1921840 | 11/1969 | Fed. Rep. of Germany | 260/562 P |
| 1141183 | 1/1969 | United Kingdom | 260/557 R |
| 1246885 | 9/1971 | United Kingdom | 260/557 R |
| 1255161 | 12/1971 | United Kingdom | 260/557 R |
| 1344735 | 1/1974 | United Kingdom | 71/98 |

OTHER PUBLICATIONS

Martin et al., CA 74:12853w (1971).
Esso, CA 79:18343e (1973).

*Primary Examiner*—Thomas A. Waltz

[57] ABSTRACT

Certain cycloalkanecarboxanilide derivatives are useful as herbicides.

5 Claims, No Drawings

CYCLOALKANECARBOXANILIDE DERIVATIVE HERBICIDES

CROSS-REFERENCE TO RELATED APPLICATIONS

This application is a continuation-in-part of Ser. No. 761,515, filed Jan. 21, 1977, now abandoned.

BACKGROUND OF THE INVENTION

Field of the Invention

This invention relates to cycloalkanecarboxanilide derivatives, their use as herbicides and to herbicidal compositions containing these cycloalkanecarboxanilides.

SUMMARY OF THE INVENTION

The present invention is directed to a new class of compounds which are useful to control plant growth. This class of compounds is characterized as amides derived from a substituted cycloalkanecarboxylic acid and certain 3,4-disubstituted anilines.

DETAILED DESCRIPTION OF THE INVENTION

The present invention is directed to new compounds, particularly useful as herbicides, having the formula

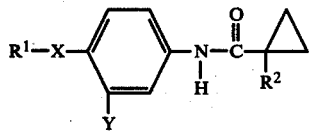

(1)

wherein
X is S, SO or $SO_2$;
Y is a halogen atom of atomic number 9 to 35, inclusive, $NO_2$, or the group -Zp-alkyl in which the alkyl portion contains from 1 to 6 carbon atoms and can be substituted by one or more halogen atoms of atomic number 9 to 35, inclusive;
Z is O, S, SO or $SO_2$;
$R^1$ is an alkyl group of from 1 to 6 carbon atoms, an alkenyl group of from 2 to 6 carbon atoms or an aryl group of from 6 to 10 carbon atoms, each optionally substituted by one or more halogen atoms having an atomic number of from 9 to 35, inclusive, or is an alkynyl group of from 3 to 4 carbon atoms, an alkoxyalkyl group in which each alkyl group contains from 1 to 6 carbon atoms, a cycloalkyl group having from 3 to 7 carbon atoms in the ring, an aralkyl group of from 7 to 9 carbon atoms optionally ring-substituted by one or two halogen atoms having an atomic number of 9 to 35, inclusive, or by alkyl of from 1 to 4 carbon atoms or when X is $SO_2$ then $R^1$ can also be $NR^3R^4$;
$R^2$ is an alkyl group of from 1 to 6 carbon atoms or a halogen atom having an atomic number of 9 to 35, inclusive;
$R^3$ and $R^4$ each independently is a hydrogen atom or an alkyl or cycloalkyl group of up to 6 carbon atoms; and
p is 0 or 1.

The compounds shown in formula I above are derivatives of substituted-cyclopropane carboxylic acids. Examples where $R^2$ in the formula is alkyl include methyl, ethyl, propyl, n-butyl and the like or where $R^2$ is a halogen atom, fluorine, chlorine or bromine.

As a general rule, the compounds preferred because of their herbicidal properties are those compounds of formula I wherein $R^2$ is methyl. The compound wherein $R^2$ is chlorine are also very active.

The group Y can be chlorine, bromine or fluorine, $NO_2$, trifluoromethyl, trifluoromethoxy, methyl, ethyl, methylsulfonyl, trifluoromethyl sulfonyl and the like. Preferred because of their herbicidal properties are compounds of formula I wherein Y is trifluoromethyl. Compounds wherein Y is methyl, ethyl, chlorine, bromine or $NO_2$ are also very active.

$R^1$ can be straight- or, preferably, branched-chain alkyl, such as methyl, ethyl, isopropyl, isobutyl, secondary-butyl, tertiary-butyl, isoamyl and the like, 2-chloroethyl, trifluoromethyl, allyl, phenyl, p-chlorophenyl, naphthyl or propargyl. Where $R^1$ is cycloalkyl it can be alkylated or linked to X by an alkylene group, for example, cyclopropyl, cyclohexyl, methylcyclopropyl, cyclopropylmethyl and the like. Additionally, $R^1$ can be such groups as methoxyethyl, benzyl, phenethyl, p-chlorobenzyl or o-methylbenzyl.

Compounds wherein $R^1$ is alkyl of 1 to 4 carbon atoms or cycloalkyl are generally preferred. Especially active are those compounds wherein $R^1$ is branched-chain alkyl, such as isopropyl or tert-butyl and the like. Ethyl, methyl and cyclopropylmethyl derivatives and ring alkylated forms are also highly active. Variations in activity of course depend on the individual combinations of $R^1$, $R^2$, X and Y.

Examples of species contemplated within the scope of the invention include:
4'-(isopropylthio)-3'-(trifluoromethyl)-1-propylcyclopropanecarboxanilide
4'-(isoamylsulfinyl)-3'-nitro-1-butylcyclopropanecarboxanilide
4'-(ethylthio)-3'-nitro-1-ethylcyclopropanecarboxanilide
4'-sulfamoyl-3'-ethyl-1-methylcyclopropanecarboxanilide
4'-(isopropylthio)-3'-methyl-1-fluorocyclopropanecarboxanilide
4'-(isobutylsulfonyl)-3'-(trifluoromethyl)-1-fluorocyclopropanecarboxanilide.

Examples of species contemplated when X is S, SO or $SO_2$ and Y is trifluoromethyl include the following:
4'-(methoxyethylthio)-3'-(trifluoromethyl)-1-methylcyclopropanecarboxanilide
4'-(allylthio)-3'-(trifluoromethyl)-1-pentylcyclopropanecarboxanilide
4'-(isoamylsulfinyl)-3'-(trifluoromethyl)-1-ethylcyclopropanecarboxanilide
4'-(isobutylsulfonyl)-3'-(trifluoromethyl)-1-butylcyclopropanecarboxanilide
4'-(cyclopropylsulfinyl)-3'-(trifluoromethyl)-1-methylcyclopropanecarboxanilide
4'-(2-fluorobenzylsulfonyl)-3'-(trifluoromethyl)-1-propylcyclopropanecarboxanilide
4'-(2-chlorobenzylthio)-3'-(trifluoromethyl)-1-methylcyclopropanecarboxanilide
4'-(4-chlorobenzylsulfinyl)-3'-(trifluoromethyl)-1-butylcyclopropanecarboxanilide
4'-(2,6-dichlorobenzylsulfonyl)-3'-(trifluoromethyl)-1-methylcyclopropanecarboxanilide
4'-(propargylthio)-3'-(trifluoromethyl)-1-ethylcyclopropanecarboxanilide 4'-(sec-butylsulfonyl)-3'-(trifluoromethyl)-1-propylcyclopropanecarboxanilide Preferred because of their herbicidal properties are compounds wherein X is S, SO or SO₂, R² is methyl and R¹ is alkyl of 1 to 4 carbon atoms such as methyl, isopropyl or isobutyl. Especially useful compounds appear to be those wherein R¹ is isopropyl or ethyl.

Examples of species contemplated where XR¹ is SO₂NR³R⁴ and Y is trifluoromethyl include the following:

4'-(N-ethyl-N-methylsulfamoyl)-3'-(trifluoromethyl)-1-methylcyclopropanecarboxanilide 4'-(tert-butylsulfamoyl)-3'-(trifluoromethyl)-1-methylcyclopropanecarboxanilide 4'-(tert-butylsulfamoyl)-3'-(trifluoromethyl)-1-methylcyclopropanecarboxanilide 4'-((1-methylcyclopropyl)sulfamoyl)-3'-(trifluoromethyl)-1-methylcyclopropanecarboxanilide Similarly, compounds of the above subclasses in which Y is halogen, especially bromine or chlorine, or methyl in place of trifluoromethyl are also highly useful subclasses of herbicides.

Compounds of formula I wherein Y is NO₂ are a useful subclass of the invention due to their relative easy and low cost of preparation as well as to their herbicidal properties.

Examples of species contemplated where Y is NO₂ include the following:

4'-(propyloxyethylsulfonyl)-3'-nitro-1-ethylcyclopropanecarboxanilide

4'-(isobutylthio)-3'-nitro-1-butylcyclopropanecarboxanilide

4'-(ethylsulfinyl)-3'-nitro-1-propylcyclopropanecarboxanilide

4'-(allylthio)-3'-nitro-1-ethylcyclopropanecarboxanilide

4'-(2,6-dichlorobenzylsulfonyl)-3'-nitro-1-propylcyclopropanecarboxanilide

Preferred because of their herbicidal properties are those compounds where Y is NO₂ and R¹ is alkyl of 2 to 4 carbon atoms. Especially useful compounds appear to be those wherein R¹ is isopropyl and X is S, SO or SO₂ as these compounds show useful crop selectivities.

Examples of species contemplated when Y is alkyl include the following:

4'-(ethylthio)-3'-methyl-1-methylcyclopropanecarboxanilide

4'-(ethylsulfonyl)-3'-methyl-1-methylcyclopropanecarboxanilide

4'-(methylthio)-3'-methyl-1-methylcyclopropanecarboxanilide

4'-(methylsulfonyl)-3'-methyl-1-methylcyclopropanecarboxanilide

4'-(isopropylthio)-3'-methyl-1-methylcyclopropanecarboxanilide

4'-(isopropylsulfonyl)-3'-methyl-1-methylcyclopropanecarboxanilide

4'-(methylthio)-3'-isopropyl-1-methylcyclopropanecarboxanilide

4'-(sulfamoyl)-3'-methyl-1-methylcyclopropanecarboxanilide

Examples of species contemplated when Y is halogen include the following:

4'-methylthio-3'-bromo-1-methylcyclopropanecarboxanilide

4'-(sulfamoyl)-3'-chloro-1-methylcyclopropanecarboxanilide

4'-(dimethylsulfamoyl)-3'-chloro-1-methylcyclopropanecarboxanilide

4'-(tert-butylsulfamoyl)-3'-chloro-1-methylcyclopropanecarboxanilide

4'-ethylthio-3'-fluoro-1-methylcyclopropanecarboxanilide

4'-(isobutylsulfonyl)-3'-fluoro-1-methylcyclopropanecarboxanilide

Cycloalkylcarboxanilides, I, can be prepared according to the following sequence of reactions:

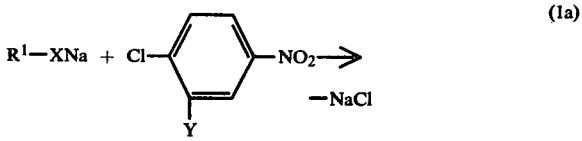

(1a)

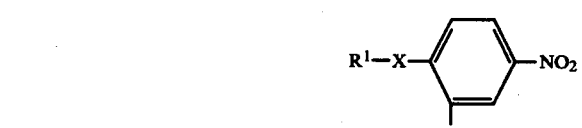

(2a)

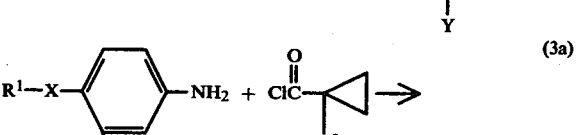

(3a)

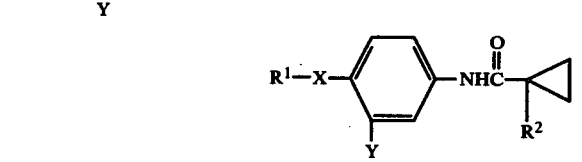

I

The appropriate sodium mercaptide compound is allowed to react with 3-substituted-4-chloronitrobenzene to give 3,4-disubstituted nitrobenzene; step (1a). In step (2a) the 3,4-disubstituted nitrobenzene is reduced to give the corresponding aniline. In step (3a) the aniline and a cycloalkylcarboxylic chloride are allowed to react to give the desired cycloalkylcarboxanilide, I.

Reaction (1a) is readily conducted by mixing the reactants in a solvent such as an alcohol, dimethyl sulfoxide or dimethylformamide at room temperature or at a moderately elevated temperature, for example up to 150° C.

The reduction of the 3,4-disubstituted nitrobenzenes, step (2a) is readily carried out in boiling water containing iron filings and up to 5% of acetic or hydrochloric acid. However, any of numerous reduction techniques that reduce an aromatic nitro group to amino are applicable here (see R. Schroter and F. Moller in Methoden der Organische Chemie. "Houben-Weyl", Vol. 11, 1, part IV, p. 341-731, Georg Thiene Verlag, Stuttgart (1957)).

The 4'-hydrocarbylsulfinyl- or sulfonyl derivatives can be prepared by treating the appropriate 4'-hydrocarbylthio derivative with 85% meta-chloroperoxybenzoic acid or similar known methods.

The acylation reaction (3a) is conducted by treating the 3,4-disubstituted aniline with a cycloalkylcarboxylic chloride in a suitable solvent such as ether, tetrahydrofuran, benzene, toluene or hexane in the presence of one molar equivalent of an organic or inorganic base that can serve as acceptor for the hydrogen chloride formed in the reaction. Organic bases such as tertiary amines (pyridine, triethylamine, collidine, N,N-dimethylaniline, ethyldiisopropylamine) or inorganic bases ($Na_2CO_3$, $NaHCO_3$, $K_2CO_3$, $CaCO_3$) may be used to trap the hydrogen chloride formed during acylation.

The cycloalkylcarboxylic chlorides used in the reaction or simple esters from which they can be generated are generally known in the art as for example in U.S. Pat. Nos. 3,277,171, 3,211,544 and South African application No. 64/1283. The 1-fluorocycloalkylcarboxylic chlorides can be readily prepared by treating 1-chlorocycloalkylcarboxylic acid ethyl ester with potassium fluoride at elevated temperatures optionally in the presence of solvents and/or phase transfer catalysts and converting the ester to acid chloride in a known manner. The 1-bromocycloalkylcarboxlic chlorides can be prepared by bromination of cycloalkylcarboxylic chlorides under refluxing conditions in a nitrogen atmosphere.

The compounds of the invention, for example, 4'-(isopropylthio)-3'-(trifluoromethyl)-1-methylcyclopropanecarboxanilide have been found to be useful for controlling undesirable plant growth. That is, certain members of the class have been found to be herbicidally effective against a wide range of plant species. Other of the class are effective only against a limited number of plants species and are considered to be selective herbicides. Some of the compounds exhibit a high degree of herbicidal activity in the control of a variety of economically important species of grasses and broad-leaved weeds. Some of the compounds are particularly useful as selective herbicides for use in certain important crops.

The invention includes plant growth regulating compositions comprising a carrier or a surface-active agent, or both a carrier and a surface-active agent, and, as active ingredient, at least one compound of Formula I. Likewise the invention also includes a method of controlling plant growth which comprises applying to the locus an effective amount of a compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example natural silicas such as diatomaceous earths; magnesium silicates, for example, attapulgites and vermiculites; aluminum silicates, for example, kaolinites, montmorillinites and micas; calcium carbonates; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquified normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 1–5% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be maufactured by agglomeration or impregnation techniques. Generally granules will contain ½–25% by weight toxicant and 0–10% by weight of additives such as stabilizers, slow release modifiers and binding agents. Emulsifiable concentrates ususally contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% w toxicant, 0.5–5% w of dispersing agents, 1–5% of surface-active agent, 0.1–10% w of suspending agents such as protective colloids and thixotropic agents, 0–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

The method of applying the compounds of this invention comprises applying a compound of formula I, ordinarily in a composition of one of the aforementioned types, to a locus or area to be protected from undesirable plant growth. The active compound, of course, is applied in amounts sufficient to exert the desired action.

The amount of compound of the invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.1 to 10.0 pounds per acre of the compound used in this invention will be satisfactory.

EXAMPLES

The manner in which the compounds of this invention can be prepared is illustrated in the following examples, which demonstrate the preparation of typical species of the invention. In these examples, the identities of all compounds, intermediates and final, were confirmed by elemental analysis, and infrared and nuclear magnetic spectral analyses. The examples are for the purpose of illustration only and should not be regarded as limiting the invention in any way.

EXAMPLE 1

4'-(Methylthio)-3'-(trifluoromethyl)-1-methylcyclopropanecarboxanilide (a) Preparation of 3-(trifluoromethyl)-4-(methylthio)-nitrobenzene To a stirred solution containing 45.1 g (0.20 mole) of 3-(trifluoromethyl)-4-chloronitrobenzene and 15 g (0.30 mole) of methyl mercaptan in 150 ml of DMSO was added dropwise at ambient temperature a solution containing 8.0 g (0.20 mole) of sodium hydroxide in 20 ml of water. This addition was exothermic to 60° C. After one hour, the reaction mixture was poured into ice water. The product was filtered and dried to give 45.0 g (95%) of yellow solid; m.p. 50° C.

(b) Preparation of 3-(trifluoromethyl)-4-(methylthio)aniline

To a mixture containing 45.0 g (0.19 mole) of (1a) in refluxing 5% aqueous acetic acid was added portionwise 61 g of iron powder. The reaction mixture was refluxed for three hours and filtered through Celite (filter aid) while hot. The cooled filtrate was extracted with ether. The ether extract was washed with 10% aqueous sodium bicarbonate, and then with water, dried over anhydrous $MgSO_4$, and concentrated under reduced pressure to give 31.8 g (81%) of product as a light yellow oil.

(c) Preparation of 4'-(methylthio)-3'-(trifluoromethyl)-1-methylcyclopropanecarboxanilide To a stirred solution containing 31.8 g (0.154 mole) of (1b) and 15.6 g (0.154 mole) of triethylamine in 200 ml of tetrahydrofuran was added dropwise over 10 minutes 18.2 g (0.154 mole) of 1-methylcyclopropanecarboxylic chloride. This addition was exothermic to 65° C. The mixture was stirred and refluxed for one hour, poured into ice water and filtered. The filter cake was washed with water and dried to give 43.5 g (98%) of product as a yellow solid; m.p. 97°-98° C.

EXAMPLE 2

4'-(Methylsulfinyl)-3'-(trifluoromethyl)-1-methylcyclopropanecarboxanilide

To a chilled (5° C.) solution containing 14.5 g (0.05 mole) of 4'-(methylthio)-3'-(trifluoromethyl)-1-methylcyclopropanecarboxanilide (prepared in Example 1 above) in 150 ml of chloroform was added dropwise over 20 minutes with stirring a solution of 10.2 g (0.05 mole) of 85% meta-chloroperoxybenzoic acid in 150 ml of chloroform. The reaction solution was allowed to equilibrate gradually to 25° C., and after 16 hours, washed well with 10% sodium carbonate and water, dried, and concentrated. The residual solid was crystallized from methanol to give 13.0 (86%) of product as a light-cream colored solid; m.p. 181°-184° C.

EXAMPLE 3

4'-(Methylsulfonyl)-3'-trifluoromethyl-1-methylcyclopropanecarboxanilide

To a stirred solution containing 7.0 g (0.024 mole) of 4'-(methylthio)-3'-(trifluoromethyl)-1-methylcyclopropanecarboxanilide (prepared in Example 1 above) in 200 ml of chloroform was added dropwise over a period of 10 minutes at ambient temperature 10.2 g (0.05 mole) of 85% meta-chloroperoxybenzoic acid. The reaction was exothermic to 50° C. The reaction mixture was stirred for 16 hours,, washed with 10% aqueous sodium carbonate and then with water. The chloroform layer was dried and concentrated to dryness. The residue was crystallized from methanol to give 7.5 g (97%) of product as a light-cream solid; m.p. 135°-138° C.

EXAMPLE 4

4'-(Isopropylthio)-3'-(trifluoromethyl)-1-methylcyclopropanecarboxanilide (a) Preparation of 4-(Isopropylthio)-3-(trifluoromethyl)nitrobenzene To a solution containing 112.8 g (0.5 mole) of 2-chloro-5-nitrobenzotrifluoride and 46 g (0.6 mole) of isopropyl mercaptan in 400 ml of DMSO was added dropwise over 0.5 hour 40 g of 50% aqueous sodium hydroxide. This addition was exothermic to 50° C. After 24 hours, the reaction mixture was poured into ice water and extracted with 3×200 ml of methylene chloride. The combined extracts were washed with water, dried and concentrated to give 132 g (99%) of product as an orange liquid.

(b) Preparation of 4-(isopropylthio)-3-(trifluoromethyl)aniline

A mixture containing 132.5 g (0.5 mole) of the nitro compound prepared as in (a) above, in 800 ml of 5% aqueous acetic acid was heated to reflux with stirring.

The heat mantle was removed and 150 g of powdered iron was added at such a rate as to maintain reflux. After completion of the addition, the mixture was stirred and refluxed for one hour, and filtered while hot. The filtrate was extracted with ether (3×300 ml). The combined extracts were washed with 10% sodium carbonate, and then with water. The dried solution was concentrated to dryness under reduced pressure to give 70.5 g (60%) of product as a yellow oil.

(c) Preparation of 4'-(isopropylthio)-3'-(trifluoromethyl)-1-methylcyclopropanecarboxanilide To a stirred solution containing 23.5 g (0.1 mole) of the aniline prepared in (b) above and 10.1 g (0.1 mole) of triethylamine in 150 ml of tetrahydrofuran was added dropwise over 5 minutes 11.9 g (0.1 mole) of 1-methylcyclopropylcarboxylic chloride. This addition was exothermic to 55° C. The mixture was refluxed for 1 hour, poured into ice water and filtered. The filter cake was recrystallized from hexane to give 25 g (79%) of product as a colorless crystalline solid, m.p. 103°–105° C.

EXAMPLES 5–28

In the manner described above, and illustrated in foregoing Examples, additional cyclopropanecarboxanilides listed in Table 1 were prepared.

Table 1

Cyclopropanecarboxanilides

| Example | X | $R^1$ | $R^2$ | % Yield | M.P., °C. |
|---|---|---|---|---|---|
| 5 | S→O | $(CH_3)_2CH-$ | $CH_3$ | 91 | 143–145 |
| 6 | S(=O)(=O) | $(CH_3)_2-$ | $CH_3$ | 75 | 140–143 |
| 7 | S | $(CH_3)_2CHCH_2-$ | $CH_3$ | 94 | 95–97 |
| 8 | S→O | $(CH_3)_2CHCH_2-$ | $CH_3$ | 67 | oil |
| 9 | S(=O)(=O) | $(CH_3)_2CHCH_2-$ | $CH_3$ | 91 | oil |
| 10 | S | $C_2H_5-$ | $CH_3$ | 86 | 68–69 |
| 11 | S→O | $C_2H_5-$ | $CH_3$ | 81 | 136–139 |
| 12 | S(=O)(=O) | $C_2H_5-$ | $CH_3$ | 83 | 140–143 |
| 13 | S | $(CH_3)_2CHCH_2CH_2-$ | $CH_3$ | 90 | 78–80 |
| 14 | S→O | $(CH_3)_2CHCH_2CH_2-$ | $CH_3$ | 69 | oil |
| 15 | S(=O)(=O) | $(CH_3)_2CHCH_2CH_2-$ | $CH_3$ | 100 | oil |
| 16 | S | $n\text{-}C_5H_{11}-$ | $CH_3$ | 88 | 60–62 |
| 17 | S→O | $n\text{-}C_5H_{11}-$ | $CH_3$ | 69 | oil |
| 18 | S(=O)(=O) | $n\text{-}C_5H_{11}-$ | $CH_3$ | 100 | oil |
| 19 | S | $CH_2=CHCH_2-$ | $CH_3$ | 48 | oil |
| 20 | S | $(CH_3)_3C-$ | $CH_3$ | 92 | 144–146 |
| 21 | S | $C_2H_5(CH_3)CH-$ | $CH_3$ | 88 | 100–102 |
| 22 | S | $n\text{-}C_6H_{13}-$ | $CH_3$ | 89 | 67–69 |
| 23 | S | $n\text{-}C_7H_{15}-$ | $CH_3$ | 89 | 60–62 |
| 24 | S | $(CH_3)_2CHCH_2-$ | $n\text{-}C_4H_9$ | 68 | 88–91 |
| 25 | S | $C_6H_5CH_2-$ | $CH_3$ | 85 | 100–102 |
| 26 | S→O | $C_6H_5CH_2-$ | $CH_3$ | 98 | oil |
| 27 | S(=O)(=O) | $C_6H_5CH_2-$ | $CH_3$ | 96 | oil |
| 28 | S | $C_2H_5-$ | $C_2H_5$ | 40 | oil |

EXAMPLE 29

4'-(Isopropylthio)-3'-nitro-1-methylcyclopropanecarboxanilide (a) Preparation of 4-(isopropylthio)-3-nitroaniline To a stirred solution containing 34.5 g (0.20 mole) of 4-chloro-3-nitroaniline and 24 g (0.30 mole) of isopropyl mercaptan in 200 ml of DMSO was added dropwise at ambient temperature a solution of 8.0 g (0.20 mole) of sodium hydroxide in 10 ml of water. The addition was exothermic to 60° and the mixture became deep red in color. After three days, the reaction mixture was poured into water and extracted with methylene chloride. The combined extracts were washed with water, dried with anhydrous MgSO4, filtered and concentrated to give 41.1 g (97%) of product as a red-brown syrup.

(b) Preparation of 4'-(isopropylthio)-3'-nitro-1-methylcyclopropanecarboxanilide To a solution containing 16.0 g (0.75 mole) of (29a) and 7.6 g (0.75 mole) of triethylamine in 150 ml of tetrahydrofuran was added dropwise with stirring 8.9 g (0.075 mole) of 1-methylcyclopropanecarboxylic chloride. This addition was exothermic to 60°. The mixture was refluxed for one hour, poured over ice water and extracted with ether. The ether extract was dried and concentrated to give 20.7 g of a dark red-brown oil. Purification by silica chromatography gave 10.5 g (48%) of product as a light-yellow solid, melting point, 92°–94°.

EXAMPLES 30–31

In the manner described in the above Example, additional cyclopropanecarboxanilides listed in Table 2 were prepared.

EXAMPLE 44

4'-(Dimethylsulfamoyl)-3'-(trifluoromethyl)-1-methylcyclopropanecarboxanilide (a) Preparation of 4-nitro-3-(trifluoromethyl)-benzenesulfonyl chloride A mixture containing 57.5 g (0.28 mole) of 4-nitro-2-(trifluoromethyl)aniline in 200 ml of concentrated hydrochloric acid was heated to 90° for 15 minutes and left stirring at ambient temperature for 18 hours. The resulting mixture was chilled to 4° and diazotized with 21.4 g (0.31 mole) of sodium nitrite in 50 ml of water. After one hour, the diazonium salt solution was added dropwise over 20 minutes and with stirring to a cold (5°–10°) solution containing 13 g of cupric chloride and 64 g of sulfur dioxide in 250 ml of glacial acetic acid. After two hours, the mixture was filtered. The filter cake was washed well with water and dried to give 68 g (84%) of product as a light tan solid; m.p. 77°–79° C.

(b) Preparation of N,N-dimethyl-4-nitro-2-(trifluoromethyl)benzenesulfonamide

To a stirred solution containing 14 g (0.05 mole) of the sulfonyl chloride prepared as in (a) above in 100 ml of tetrahydrofuran was added through a gas-inlet tube an excess of anhydrous dimethylamine causing the internal temperature to rise to 60°. The mixture was stirred at ambient temperature for ½ hour, poured into 500 ml of ice water and filtered. The filter cake was

Table 2
Cyclopropanecarboxanilides

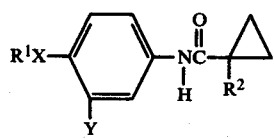

| Example | X | Y | R¹ | R² | % Yield | M.P., °C. |
|---|---|---|---|---|---|---|
| 30 | S→O | NO₂ | (CH₃)₂CH— | CH₃ | 73 | 143–145 |
| 31 | S(→O)(→O) | NO₂ | (CH₃)₂CH— | CH₃ | 90 | 103–105 |
| 32 | S | CF₃ | C₂H₅— | Cl | 80 | 56–58 |
| 33 | S | CF₃ | CH₂=CHCH₂— | Cl | 60 | oil |
| 34 | S | SO₂CH₃ | C₂H₅— | CH₃ | 56 | 130–134 |
| 35 | S | CF₃ | (CH₃)₂CH— | Cl | 60 | 62–64 |
| 36 | S(→O)(→O) | CF₃ | CH₃CH₂(CH₃)CH— | | 96 | oil |
| 37 | S | Br | (CH₃)₂CH— | CH₃ | 44 | 82–88 |
| 38 | S | Br | C₂H₅— | CH₃ | 53 | 124–125 |
| 39 | S | Br | CH₃CH₂(CH₃)CH— | CH₃ | 70 | 90 |
| 40 | S(→O)(→O) | Br | CH₃CH₂(CH₃)CH— | CH₃ | 76 | 105 |
| 41 | S(→O)(→O) | Br | (CH₃)₂CH— | CH₃ | 85 | 128 |
| 42 | S(→O)(→O) | Br | C₂H₅— | CH₃ | 8 | 105 |
| 43 | S→O | Br | C₂H₅— | CH₃ | 27 | 129 | washed with water and dried to give 14 g (94%) of product as a light tan solid; m.p. 95°–97° C.

(c) Preparation of 4-(dimethylsulfamoyl)-3-(trifluoromethyl)aniline

To a heated mixture containing 13.5 g (0.045 mole) of the amide prepared as in (b) above in 250 ml of 5% acetic acid was added portionwise and with stirring 12 g of iron powder. The mixture was refluxed for ½ hour. The mixture was filtered while hot and the cooled filtrate was extracted with ether. The ether extract was washed with aqueous sodium bicarbonate, dried, concentrated and recrystallized from ether-hexane (1:2) to give 10.1 g (83%) of product as a colorless solid; m.p. 140°–142° C.

(d) Preparation of 4'-(dimethylsulfamoyl)-3'-(trifluoromethyl)-1-methylcyclopropane-carboxanilide To a solution of 6.7 g (0.025 mole) of the aniline prepared as in (c) above and 2.5 g of triethylamine in 50 ml of tetrahydrofuran was added dropwise 3.0 g (0.025 mole) of 1-methylcyclopropanecarboxylic chloride. The mixture was refluxed for one hour, poured into ice water, filtered and recrystallized from methanol to give 7.5 g (86%) of product as a white crystalline solid; m.p. 153°–156° C.

EXAMPLE OF HERBICIDAL ACTIVITY

The pre-emergence herbicidal activity of the compounds of the invention was evaluated by planting seeds of garden cress, downey brome, wild mustard (or sicklepod), velvet leaf, soybean, wheat, and cotton in test tubes, nominally measuring 25×200 millimeters, containing soil treated with the test compound at the rates of 0.01 and 1 mg per tube designated in Table I at Rates I and II, respectively. The planted soil was held under controlled conditions of temperature, moisture, and light for 13 to 14 days. The amount of germination and growth in each tube were evaluated on a 0 to 9 scale, 0 rating indicating no effect, 9 death of the seedlings or no germination.

The post-emergence activity of the compounds of this invention was evaluated by spraying 7-day old crabgrass plants, 10-day old pigweed plants, 7-day old downey brome plants, 10-day old wild mustard (or 7-day old sicklepod), 10-day old velvet leaf, 14-day old soybean plants, 7-day old wheat and 14-day old cotton plants to runoff with a liquid formulation of the test compound at the rates of 0.62 milliliter of an 0.05% solution designated Rate I in Table I, and 0.56 milliliter of an 0.5% solution designated Rate II in Table I. The sprayed plants were held under controlled conditions for 10 to 11 days and the effect of the test compound was then evaluated visually, the results being rated on the 0 to 9 scale described above.

The results of the pre- and post-emergence tests are summarized in Table I.

The herbicidal activity of the compounds of this invention was further determined with respect to several common species of weeds, by spraying a formulation of the test compound on the soil in which the weed seeds had been planted (pre-emergence test) or onto the foliage of the plants (post-emergence test). In each series of tests, the plants were grown in narrow trays and sprayed with chemical. The solution of the test compound was sprayed over the tray, from one end to the other, the concentration of the test compound in the formulation varying logarithmically from a higher value at one end of the band to a lower value at the other end of the band. The effect of the test compound was evaluated visually and reported as the nominal rate of application, in pounds of test compound per acre of the soil band, at which 90% inhibition of the growth of the weeds occurred, this being referred to as the 90% growth inhibition, of $GI_{90}$, dosage. Results of the pre-emergence and post-emergence tests, as well as the weed species involved, are set out in Tables II and III.

TABLE I
RESULTS OF THE HERBICIDE ACTIVITY SCREEN

| | PRE-EMERGENCE (SOIL) | | | | | | | POST-EMERGENCE (FOLIAR) | | | | | | | |
|---|---|---|---|---|---|---|---|---|---|---|---|---|---|---|---|
| | Garden Cress | Downey Brome | Wild Mustard | Velvet Leaf | Soybean | Wheat | Cotton | Crabgrass | Pigweed | Downey Brome | Wild Mustard | Velvet Leaf | Soybean | Wheat | Cotton |
| Example | I / II | I / II | I / II | I / II | II | II | II | I / II | I / II | I / II | I / II | I / II | II | II | II |
| 1 | 3 / 9 | 0 / 9 | 8 / 9 | 0 / 7 | 5 | 7 | 5 | 4 / 0 | 8 / 7 | 1 / 0 | 7 / 0 | 7 / 3 | 8 | 6 | 0 / 7 |
| 2 | 9 / 9 | 3 / 9 | 5 / 9 | 7 | 7 | 7 | 0 | 0 / 6 | 8 / 0 | 2 / 6 | 4 / 7 | 5 | 4 | 6 | 7 |
| 3 | 9 / 9 | 6 / 6 | 6 / 9 | 9 | 7 | 6 | 7 / 0 | 1 / 1 | 8 / 5 | 1 / 1 | 9 / 5 | 8 / 9 | 7 | 5 | 7 |
| 5 | 9 / 9 | 6 / 6 | 6 / 9 | 9 | 9 | 7 | 7 / 6 | 4 / 4 | 9 / 9 | 5 / 4 | 9 / 5 | 9 / 9 | 6 | 6 | 7 |
| 6 | 9 / 0 | 6 / 0 | 6 / 0 | 9 / 0 | 9 | 7 | 6 / 0 | 6 / 6 | 9 / 9 | 9 / 4 | 9 / 9 | 9 / 8 | 6 | 6 | 7 |
| 7 | 0 / 9 | 0 / 5 | 0 / 9 | 0 / 5 | 0 | 0 | 0 | 8 / 2 | 9 / 9 | 5 / 3 | 9 / 7 | 8 / 8 | 8 | 4 | 8 |
| 8 | 9 / 8 | 7 / 0 | 7 / 9 | 9 / 7 | 9 | 7 | 5 | 4 | 7 / 7 | 9 / 9 | 5 / 0 | 9 / 8 | 8 / 8 | 8 | 7 | 8 |
| 9 | | | | | | | | | | | | | | | |
| 17 | 9 / 7 | 7 / 0 | 7 / 9 | 9 / 0 | 9 | 6 | 4 | 6 | 7 / 0 | 9 / 0 | 5 / 0 | 9 / 7 | 8 / 3 | 5 | 5 | 9 |

TABLE I-continued
RESULTS OF THE HERBICIDE ACTIVITY SCREEN

| Cmpd | | PRE-EMERGENCE (SOIL) | | | | | | | POST-EMERGENCE (FOLIAR) | | | | | | |
|---|---|---|---|---|---|---|---|---|---|---|---|---|---|---|---|
| | | Garden Cress | Downey Brome | Wild Mustard | Velvet Leaf | Soybean | Wheat | Cotton | Crabgrass | Pigweed | Downey Brome | Wild Mustard | Velvet Leaf | Soybean | Wheat | Cotton |
| 18 | a | 9 | 4 | 9 | 9 | 1 | 1 | 0 | 0 | 5 | 4 | 9 | 8 | 8 | 4 | 9 |
| | b | 6 | 0 | 9 | 0 | | | | 0 | 0 | 2 | 8 | 8 | | | |
| 14 | a | 9 | 3 | 9 | 7 | 1 | 1 | 0 | 0 | 1 | 3 | 9 | 9 | 9 | 8 | 8 |
| | b | 9 | 0 | 9 | | | | | 0 | 1 | 0 | 8 | 8 | | | |
| 15 | a | 9 | 8 | 9 | 9 | 5 | 5 | 0 | 2 | 7 | 3 | 8 | 9 | 9 | 4 | 9 |
| | b | 8 | 0 | 9 | 3 | | | | 0 | 3 | 4 | 9 | 9 | | | |
| 19 | a | 8 | 4 | 9 | 9 | 2 | 2 | 0 | 6 | 9 | 7 | 9 | 9 | 9 | 8 | 9 |
| | b | 0 | 0 | 2 | 0 | | | | 8 | 9 | 5 | 9 | 9 | | | |
| 10 | a | 9 | 0 | 9 | 0 | 0 | 0 | 0 | 9 | 9 | 8 | 9 | 9 | 8 | 8 | 9 |
| | b | 9 | 5 | 8 | 8 | | | | 9 | 9 | 8 | 9 | 9 | | | |
| 11 | a | 9 | 7 | 9 | 9 | 8 | 6 | 0 | 9 | 9 | 9 | 9 | 9 | 7 | 3 | 8 |
| | b | 9 | 7 | 9 | 9 | | | | 2 | 9 | 9 | 9 | 9 | | | |
| 12 | a | 9 | 7 | 9 | 9 | 8 | 7 | 7 | 8 | 9 | 9 | 9 | 9 | 5 | 2 | 9 |
| | b | 9 | 8 | 9 | 9 | | | | 2 | 9 | 8 | 9 | 9 | | | |
| 24 | a | 9 | 8 | 9 | 9 | 8 | 8 | 0 | 8 | 9 | 9 | 9 | 9 | 5 | 1 | 8 |
| | b | 0 | 0 | 0 | 0 | | | | 6 | 3 | 2 | 8 | 8 | | | |
| 22 | a | 1 | 0 | 0 | 0 | 0 | 0 | 0 | 6 | 9 | 2 | 9 | 8 | 8 | 2 | 9 |
| | b | 0 | 0 | 0 | 0 | | | | 7 | 4 | 0 | 8 | 3 | | | |
| 23 | a | 0 | 0 | 0 | 0 | 0 | 0 | 0 | 8 | 9 | 0 | 9 | 7 | 7 | 2 | 9 |
| | b | 0 | 0 | 0 | 0 | | | | 5 | 7 | 0 | 7 | 5 | | | |
| 21 | a | 0 | 0 | 0 | 0 | 0 | 0 | 0 | 5 | 7 | 9 | 7 | 8 | 8 | 2 | 9 |
| | b | 5 | 0 | 0 | 0 | | | | 7 | 4 | 0 | 8 | 8 | | | |
| 20 | a | 8 | 0 | 8 | 0 | 0 | 0 | 0 | 8 | 9 | 5 | 8 | 9 | 9 | 2 | 9 |
| | b | 0 | 0 | 0 | 0 | | | | 0 | 0 | 5 | 6 | 3 | | | |
| 13 | a | 0 | 0 | 0 | 0 | 0 | 0 | 0 | 0 | 7 | 5 | 7 | 9 | 8 | 3 | 4 |
| | b | 0 | 0 | 0 | 0 | | | | 6 | 3 | 1 | 9 | 8 | | | |
| 30 | a | 1 | 0 | 0 | 0 | 0 | 0 | 0 | 7 | 8 | 1 | 9 | 8 | 8 | 0 | 9 |
| | b | 3 | 3 | 4 | 0 | | | | 0 | 0 | 0 | 4 | 0 | | | |
| 31 | a | 9 | 7 | 9 | 9 | 0 | 5 | 0 | 2 | 9 | 0 | 8 | 9 | 1 | 0 | 6 |
| | b | 9 | 2 | 9 | 6 | | | | 0 | 9 | 5 | 9 | 9 | | | |
| 29 | a | 9 | 7 | 9 | 9 | 1 | 0 | 0 | 6 | 9 | 7 | 9 | 9 | 2 | 0 | 8 |
| | b | 3 | 0 | 3 | 3 | | | | 7 | 8 | 3 | 8 | 9 | | | |
| 25 | a | 6 | 0 | 8 | 7 | 0 | 0 | 0 | 9 | 9 | 6 | 9 | 9 | 2 | 0 | 8 |
| | b | 0 | 0 | — | 0 | | | | 7 | 9 | 5 | — | 6 | | | |
| 26 | a | 0 | 0 | — | 0 | 5 | 0 | 0 | 9 | 9 | 5 | — | 9 | 4 | 0 | 5 |
| | b | 0 | 0 | — | 0 | | | | 2 | 8 | 3 | — | 9 | | | |
| 27 | a | 8 | 2 | — | 6 | 0 | 0 | 0 | 8 | 9 | 7 | — | 9 | 3 | 0 | 3 |
| | b | 2 | 0 | — | 0 | | | | 1 | 8 | 4 | — | 3 | | | |
| 28 | a | 9 | 0 | — | 3 | 0 | 0 | 0 | 6 | 9 | 7 | — | 4 | 0 | 0 | 0 |
| | b | 2 | 0 | — | 0 | | | | 0 | 4 | 0 | — | 0 | | | |
| 32 | a | 2 | 0 | — | 0 | 0 | 0 | 0 | 7 | 7 | 3 | — | 7 | 5 | 0 | 0 |
| | b | 2 | 0 | — | 0 | | | | 3 | 8 | 2 | — | 5 | | | |
| 33 | a | 9 | 0 | — | 0 | 0 | 0 | 0 | 8 | 9 | 5 | — | 7 | 1 | 0 | 2 |
| | b | 0 | 0 | — | 0 | | | | 3 | 6 | 0 | — | 4 | | | |
| 36 | a | 2 | 0 | — | 0 | 0 | 0 | 9 | 8 | 8 | 7 | — | 9 | 2 | 0 | 0 |
| | b | — | 7 | — | 9 | | | | 9 | 9 | 7 | 9 | 9 | | | |
| 37 | a | — | 8 | — | 9 | — | 7 | 0 | 9 | 9 | 7 | 9 | 9 | 9 | 7 | 9 |
| | b | 7 | 0 | 0 | 8 | | | | 8 | 9 | 0 | 9 | 9 | | | |
| 38 | a | 8 | 4 | 0 | 8 | 2 | 2 | 0 | 8 | 9 | 9 | 9 | 9 | 9 | 0 | 8 |
| | b | 7 | 0 | 0 | 8 | | | | 7 | 9 | 4 | 9 | 9 | | | |
| | | 8 | 4 | 3 | 9 | 0 | 5 | 0 | 8 | 9 | 4 | 9 | 9 | 9 | 4 | 2 |

TABLE I-continued
RESULTS OF THE HERBICIDE ACTIVITY SCREEN

| | PRE-EMERGENCE (SOIL) | | | | | | | POST-EMERGENCE (FOLIAR) | | | | | | | |
|---|---|---|---|---|---|---|---|---|---|---|---|---|---|---|---|
| Example | Garden Cress | Downey Brome | Wild Mustard | Velvet Leaf | Soybean | Wheat | Cotton | Crabgrass | Pigweed | Downey Brome | Wild Mustard | Velvet Leaf | Soybean | Wheat | Cotton |
| 39 | 0 | 0 | 0 | 0 | | | | 8 | 8 | 0 | 4 | 9 | | | |
| 40 | 6 | 2 | 0 | 7 | 0 | 0 | 0 | 9 | 9 | 6 | — | 9 | 9 | 7 | 3 | 8 |
| 41 | 7 | 7 | 3 | 9 | 2 | 2 | 0 | 9 | 9 | 6 | 9 | 9 | 8 | 0 | 8 |
| 42 | 7 | 7 | 8 | 9 | 6 | 2 | 0 | 9 | 9 | 7 | 9 | 9 | 9 | 4 | 8 |
| 43 | 7 | 7 | 6 | 7 | 5 | 8 | 0 | 9 | 9 | 7 | 9 | 8 | 9 | 3 | 8 |
|    | 8 | 4 | 6 | 8 | 5 | 5 | 2 | 9 | 9 | 5 | 9 | 8 | 9 | 4 | 7 |

TABLE II
RESULTS OF POST-EMERGENCE FOLIAR APPLICATON HERBICIDE RATE EVALUATION SCREEN
$GI_{90}$

| Example | Yellow Foxtail | Fall Panicum | Crabgrass | Pigweed | Mustard | Velvet Leaf | Downey Brome | Barnyard grass |
|---|---|---|---|---|---|---|---|---|
| 22 | 1.0 | >2.0 | 0.52 | 0.24 | <0.22 | 2.0 | >2.0 | 1.34 |
| 23 | >2.0 | >2.0 | 1.0 | <0.22 | 0.22 | >2.0 | >2.0 | 1.5 |
| 21 | 1.36 | 1.0 | 1.36 | 0.26 | <0.22 | 0.3 | >2.0 | >2.0 |
| 13 | 1.36 | >2.0 | 1.34 | 0.22 | 0.22 | 1.0 | >2.0 | 1.36 |
| 18 | >2.0 | >2.0 | 1.5 | 0.22 | <0.22 | 0.7 | >2.0 | >2.0 |
| 14 | 0.7 | 0.7 | 1.34 | 0.4 | 0.22 | <0.22 | >2.0 | 0.7 |
| 15 | 0.84 | 1.36 | 0.70 | 0.64 | <0.22 | <0.22 | 1.34 | 0.26 |
| 1 | 1.64 | 1.34 | 2.0 | >2.0 | 1.0 | 1.0 | >2.0 | >2.0 |
| 3 | >2.0 | >2.0 | >2.0 | 1.12 | 1.64 | 1.64 | >2.0 | >2.0 |
| 4 | >0.22 | 0.52 | 0.26 | <0.22 | <0.22 | 0.3 | 1.12 | 0.22 |
| 6 | 0.7 | 0.92 | 0.64 | <0.22 | 1.36 | 0.92 | >2.0 | 0.84 |
| 7 | <0.22 | 0.7 | 2.0 | <0.22 | <0.22 | <0.22 | 2.0 | 0.22 |
| 8 | 0.76 | 0.76 | 2.0 | 0.58 | 0.76 | 0.48 | >2.0 | 0.7 |
| 9 | 0.76 | 0.4 | 1.34 | <0.22 | 0.36 | <0.22 | 2.0 | 0.52 |

(The symbol < means "less than".)
(The symbol > means "greater than".)

TABLE III
RESULTS OF PRE-EMERGENCE SOIL APPLICATION HERBICIDE RATE EVALUATION SCREEN

| Example | Soil Type | Yellow Foxtail | Fall Panicum | Crabgrass | Pigweed | Wild Mustard | Velvet Leaf | Downey Brome | Barnyard grass |
|---|---|---|---|---|---|---|---|---|---|
| 1 | Webster | >2.0 | >2.0 | >.20 | 1.34 | >2.0 | >2.0 | >2.0 | >2.0 |
|   | Hanford | >1.0 | >1.0 | >1.0 | 0.58 | 0.7 | >1.0 | >1.0 | >1.0 |
| 3 | Webster | >2.0 | >2.0 | >2.0 | 1.5 | >2.0 | >2.0 | >2.0 | >2.0 |
|   | Hanford | >1.0 | >1.0 | >1.0 | 0.92 | 0.7 | >1.0 | >1.0 | >1.0 |
| 4 | Webster | >2.0 | <1.0 | >2.0 | <1.0 | <1.0 | >2.0 | >2.0 | >2.0 |
|   | Hanford | >1.0 | 0.44 | >1.0 | <0.22 | 0.36 | >1.0 | >1.0 | 1.0 |
|   | Webster | >2.0 | 1.34 | >2.0 | <1.0 | <1.0 | 1.8 | >2.0 | >2.0 |
|   | Hanford | 0.92 | 1.0 | >1.0 | 0.22 | <0.22 | 0.52 | 0.58 | 0.92 |
| 8 | Webster | >2.0 | 1.12 | >2.0 | <1.0 | <1.0 | 1.36 | >2.0 | >2.0 |
|   | Hanford | >1.0 | 1.0 | >1.0 | 0.7 | 0.3 | 0.76 | >1.0 | >1.0 |
| 9 | Webster | >2.0 | <1.0 | >2.0 | <1.0 | <1.0 | 1.64 | >2.0 | >2.0 |
|   | Hanford | <1.0 | 0.52 | >1.0 | 0.26 | 0.7 | 0.76 | >1.0 | >1.0 |

(The symbol < means "less than".)
(The symbol > means "greater than".)

In many instances the compounds of the invention possess a selective action against weeds in crop plant cultures. For example, control of grasses and broadleaf weeds in grain crops such as wheat can be achieved by post-emergence application of such compounds of the invention as:

4′-(isobutylsulfonyl)-3′-(trifluoromethyl)-1-methylcyclopropanecarboxanilide; or 4′-(ethylthio)-3′-(trifluoromethyl)-1-methylcyclopropanecarboxanilide.

Control of weeds in soybean crops is an example of the selective herbicidal activity of 4′-(isopropylthio)-3′-(trifluoromethyl)-1-methylcyclopropanecarboxanilide.

The above species and/or other species of the invention have likewise shown post-emergence, and in some cases, pre-emergence selective activity for peanuts, grain sorghum, cotton, rice, corn, alfalfa or the like.

We claim:

1. A compound of the formula

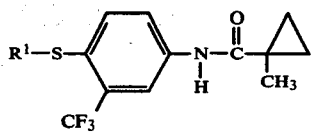

wherein $R^1$ is ethyl or isopropyl.

2. A compound according to claim 1 wherein $R^1$ is ethyl.

3. A compound according to claim 1 wherein $R^1$ is isopropyl.

4. A herbicidal composition comprising a herbicidally effective amount of a compound according to claim 1 and at least one surface-active agent or carrier.

5. A method for controlling undesirable plant growth at a locus to be protected which comprises applying to the locus to be protected a herbicidally effective amount of a compound according to claim 1 or a composition thereof.

* * * * *